United States Patent

Zhou et al.

(10) Patent No.: US 6,517,694 B1
(45) Date of Patent: Feb. 11, 2003

(54) YTTRIA-STABILIZED ZIRCONIA MEMBRANE ELECTRODE

(75) Inventors: Xiangyang Zhou, State College, PA (US); Serguei Lvov, State College, PA (US); Sergey M. Ulyanov, State College, PA (US)

(73) Assignee: Penn State Research Foundation, University Park, PA (US)

( * ) Notice: Subject to any disclaimer, the term of this patent is extended or adjusted under 35 U.S.C. 154(b) by 0 days.

(21) Appl. No.: 09/856,058

(22) PCT Filed: Nov. 23, 1999

(86) PCT No.: PCT/US99/27767

§ 371 (c)(1),
(2), (4) Date: May 17, 2001

(87) PCT Pub. No.: WO00/31525

PCT Pub. Date: Jun. 2, 2000

Related U.S. Application Data

(60) Provisional application No. 60/109,977, filed on Nov. 25, 1998.

(51) Int. Cl.[7] .................................................. G01N 27/26
(52) U.S. Cl. ........................ 204/433; 204/435; 204/421; 204/291; 29/746
(58) Field of Search ................................ 204/433, 435, 204/421, 291; 29/746

(56) References Cited

U.S. PATENT DOCUMENTS

| | | | | |
|---|---|---|---|---|
| 4,264,424 A | * | 4/1981 | Niedrach | 204/435 |
| 4,576,667 A | * | 3/1986 | Taylor et al. | 156/89 |
| 5,238,553 A | * | 8/1993 | Hettiarachchi et al. | 204/435 |
| 5,556,534 A | * | 9/1996 | Alcock et al. | 204/433 |
| 6,357,284 B1 | * | 3/2002 | Kim et al. | 204/435 |

* cited by examiner

*Primary Examiner*—Bruce F. Bell
(74) *Attorney, Agent, or Firm*—John J. Elnitski, Jr.

(57) ABSTRACT

The present invention is an improved yttria-stabilized zirconia electrode having a ceramic tube (12). The electrode is improved by replacing the method of sealing the electrode with an epoxy seal (24) and filling the tube with a ceramic glue (42) without completely filling the tube. The ceramic glue is added in a small amount and the ceramic glue is heated in the tube before a next small amount of ceramic glue is added, until the final amount of ceramic glue is added and heated. Also, an area of cover on a wire (18) in an area between a top of the ceramic glue and a top of the tube is partially removed. A sealing glue above the top of the ceramic glue that adheres to the wire at the removed area of the cover, adheres to the tube and seals the top of the tube. Finally, an outside portion of the wire which extends beyond the top of the tube is gripped with a CONAX fitting (26), instead of the fitting gripping the tube.

22 Claims, 6 Drawing Sheets

Potential of hydrogen (Pt) electrode vs. a flow-through external pressure balanced reference electrode (FTEPBRE) as function of time. Note that the potential difference between Solution 1 (0.0102 molal HCl) and Solution 3 (0.00114 molal HCl) is (102±4) mV. Experimental conditions: 350°C, 248 bars, flow rate, 1.00 ml/min.

Potential of YSZ pH sensing electrode vs. FTEPBRE as a function of time. Note that the potential difference between Solution 1 (0.0102 molal HCl) and Solution 2 (0.00114 molal HCl) is (104.5±2)mV; this value is close to the value obtained for the hydrogen electrode under the same conditions.

YTTRIA-STABILIZED ZIRCONIA MEMBRANE ELECTRODE

This application claims priority to U.S. Provisional Application No. 60/109,977 filed Nov. 25, 1998, which is herein incorporated by reference.

BACKGROUND

High temperature and high pressure aqueous solutions have an enormous number of applications in sciences and industries, including geosciences, synthesis and deposition of ceramics, supercritical water oxidation, fossil, nuclear, and geothermal power generation, pulp and paper production, and chemical productions. Potentiometric and pH measurements provide important information for studying thermodynamics and electrochemistry in high temperature aqueous solutions and in-situ monitoring and control of physical and chemical processes, e.g. speciation and corrosion, in industrial systems. More and more electrochemical sensors are used in industries. However, there are only a few devices having pH sensing electrodes for use during measurement in high temperature environments. Currently, the only primary and reliable pH sensing electrode available for use at high subcritical and supercritical temperatures (>374° C.) is the Yttria-Stabilized Zirconia (YSZ) membrane electrode.

Two typical designs of YSZ electrodes used in the laboratory are shown in FIGS. 1 and 2. The electrode 10 of FIG. 1 is a YSZ tube 12 with a closed tip 14 and an open top 22. The closed tip 14 of the tube 12 is filled with a small amount of Hg|HgO paste 16. A Platinum (Pt) wire 18 that is partially covered with a shrinkable PTFE tube is placed in the tube 12, whereby the uncovered portion of the PT wire 18 is inserted into the Hg|HgO paste 16. The tube 12 is then filled with zirconia sand 20. The Pt wire 18 is used to provide electrical contact. The open top 22 of the tube 12 is typically sealed with epoxy 24 over the sand 20. The whole tube 12 is fitted into a CONAX fitting 26 at the top 22 of the tube 12 whereby the CONAX fitting 26 is a tube fitting used for gripping and sealing a tube. The wall of the tube 12 is the boundary separating the high pressure fluid (typically 300 bars) and the low pressure outside of the system. Under high pressures, the tube 12 will break, especially at the point where the CONAX fitting 26 grips t he YSZ tube 12. The electrode 27 of FIG. 2 is designed to eliminate breaking at the gripping location of the CONAX fitting 26. The electrode 27 utilizes complex techniques of joining ceramics to metals, such as brazing, to produce a tube 12 having an upper portion 28 of metal and a lower portion 30 of ceramic. Thus, allowing the CONAX fitting 26 to grip the metal upper portion 28 part of the tube 12. The problem with the metal-ceramic electrode 27 of FIG. 2 is that the metal-ceramic joint is normally not strong enough to sustain high temperatures and high pressures for a long period of time. Other methods of joining metals to ceramics have been tried or proposed. However, these methods are either not reliable or extremely costly.

The object of the present invention is to provide a more reliable YSZ membrane electrode.

SUMMARY OF THE INVENTION

The present invention is an improved yttria-stabilized zirconia electrode having a ceramic tube. The electrode is improved by replacing the method of sealing the electrode with an epoxy seal and filling the tube with a ceramic glue without completely filling the tube. The ceramic glue is added in a small amount and the ceramic glue is heated in the tube before the next small amount of ceramic glue is added, until the final amount of ceramic glue is added and heated. Also, an area of cover on a wire in an area between a top of the ceramic glue and a top of the tube is partially removed. A sealing glue above the top of the ceramic glue that adheres to the wire at the removed area of the cover, adheres to the tube and seals the top of the tube. Finally, an outside portion of the wire which extends beyond the top of the tube is gripped with a CONAX fitting, instead of the fitting gripping the tube.

DETAILED DESCRIPTION OF THE INVENTION

Figure 1:
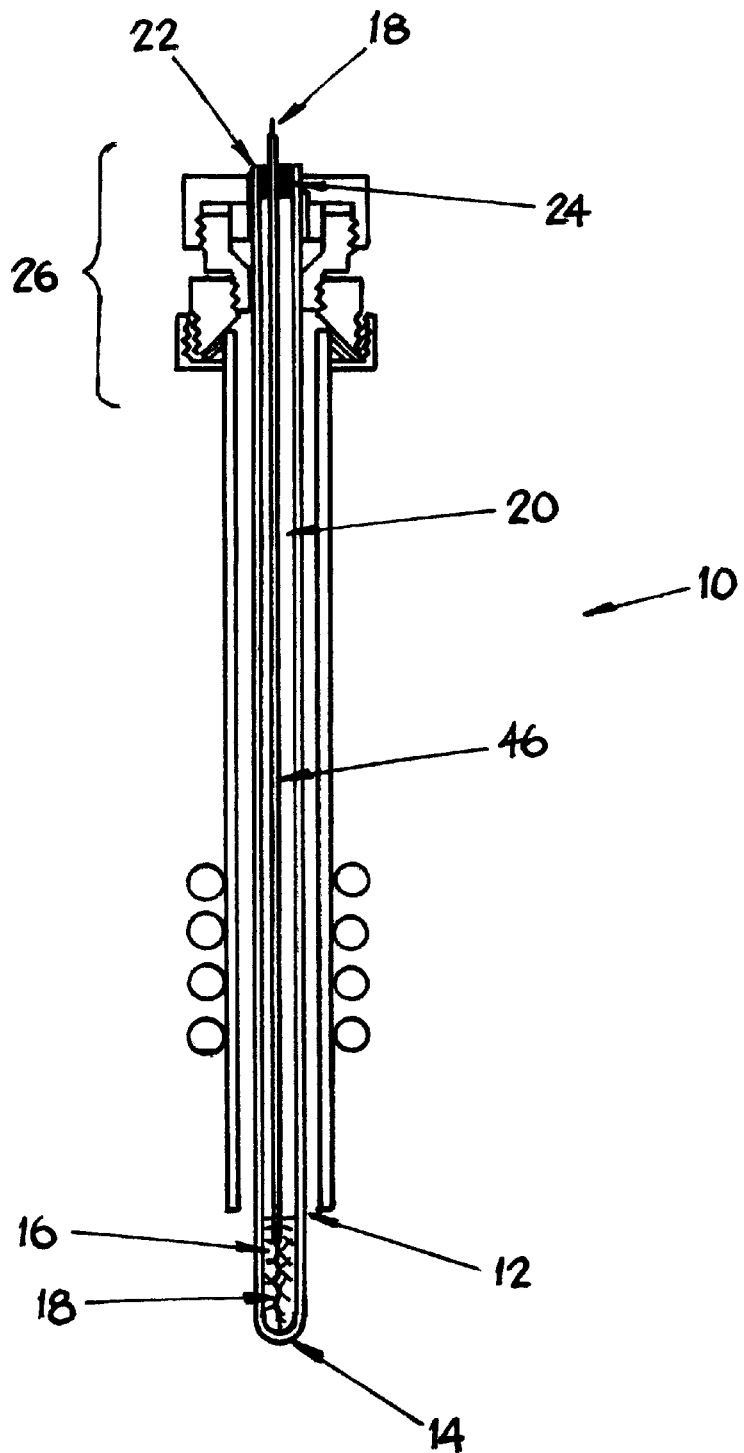
FIG. 1 is a cross-sectional view of a prior art design.
Figure 2:
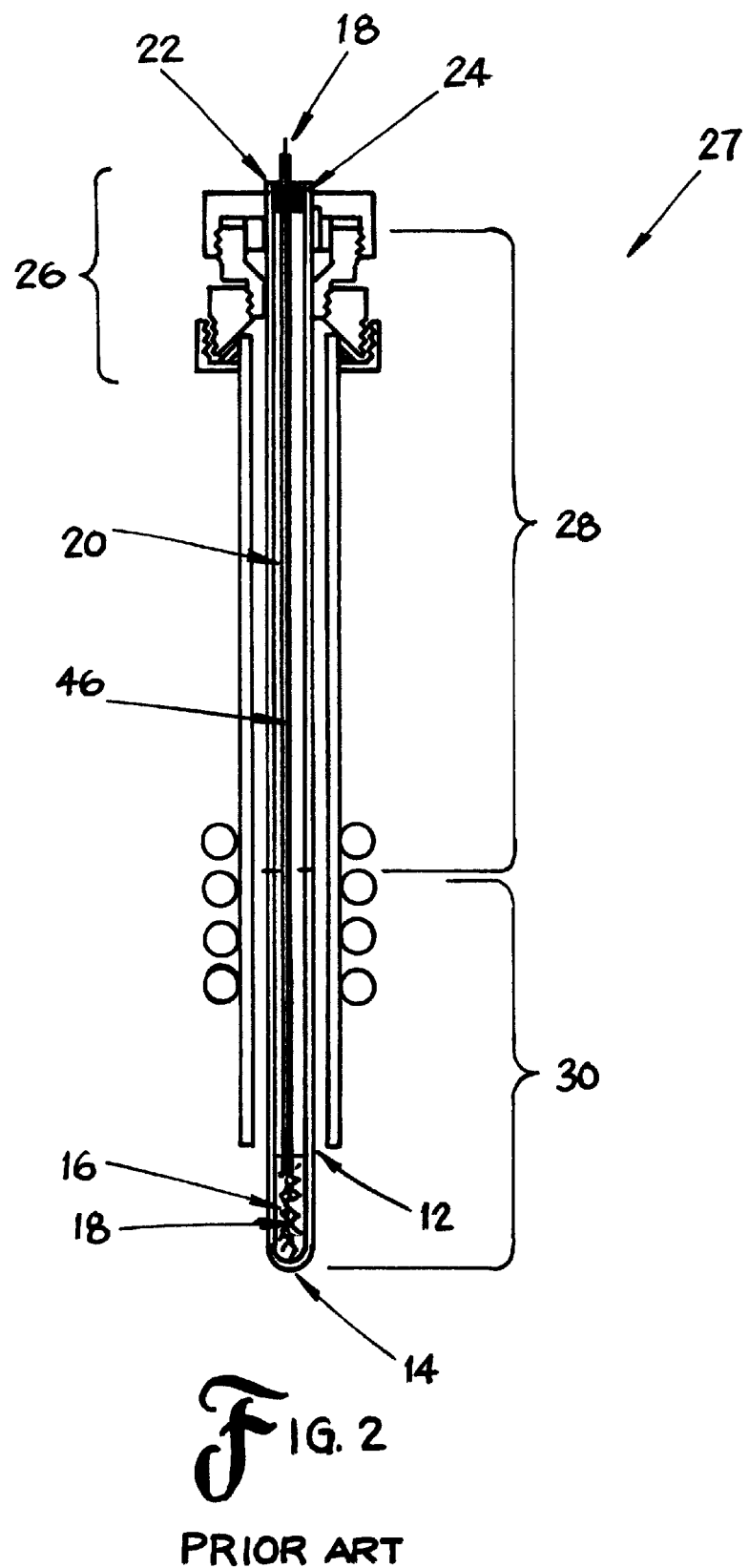
FIG. 2 is a cross-sectional view of another prior art design.
Figure 3:
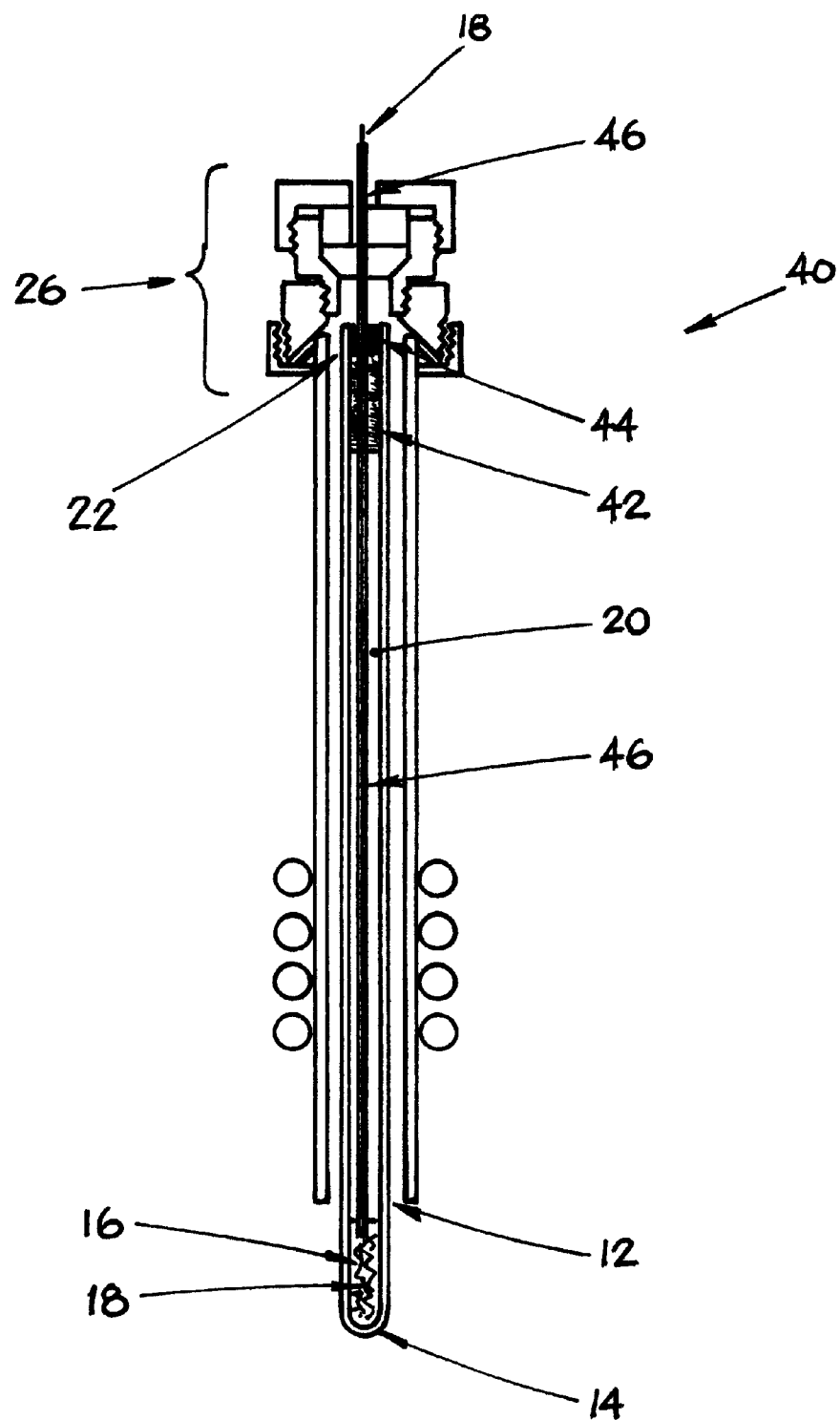
FIG. 3 is a cross-sectional view of an electrode according to the present invention.

The present invention is an improved YSZ pH sensing electrode 40, as shown in FIG. 3. There are two differences which overcome the deficiencies of the current electrodes available. First, on top of the zirconia sand 20, a ceramic glue 42 is instead of the epoxy 24. Whereby, the sand 20 is not filled to its usually height to allow for more ceramic glue 42. The ceramic glue 42 should be filled in the tube 12 using the following the steps: 1) add one centimeter of glue 42; 2) preheat the tube at 120° C. for 24 hours; 3) heat the tube at 600° C. for 5 hours; 4) add another centimeter of glue 42; 5) preheat the tube at 120° C. for 24 hours; and 6) heat the tube at 600° C. for 5 hours. The ceramic glue 42 should only partially fill the tube 12 as shown in FIG. 3 to allow room for Chembond glue 44 that is also shown. The Chembond glue 44 is a glue which adheres to polymers and ceramics. Following the above-described procedure allows the glue 42 to strongly adhere to the inside wall of the YSZ tube 12. Second, the PTFE cover 46 on the Pt wire 18 is etched with active sodium in the area between the of the ceramic glue 42 and the top 22 of the tube 12 to remove some of the PTFE cover 46 on the Pt wire 18. This area of the tube 12 is then filled with the Chembond glue 44 to seal the tube 12. The two above-mentioned procedures allow a tight bond to form between the tube 12 and the ceramic glue 42 and between the Pt wire 18 and the Chembond glue 44 and tube 12. The CONAX fitting 26 is fitted to grip PTFE cover 46 of the Pt wire 18 which extends from the top 22 of the tube 12 instead of the tube 12 itself, in contrast to the current available electrodes. The whole ceramic tube 12 now ready for use in high pressure fluid.

Figure 4:
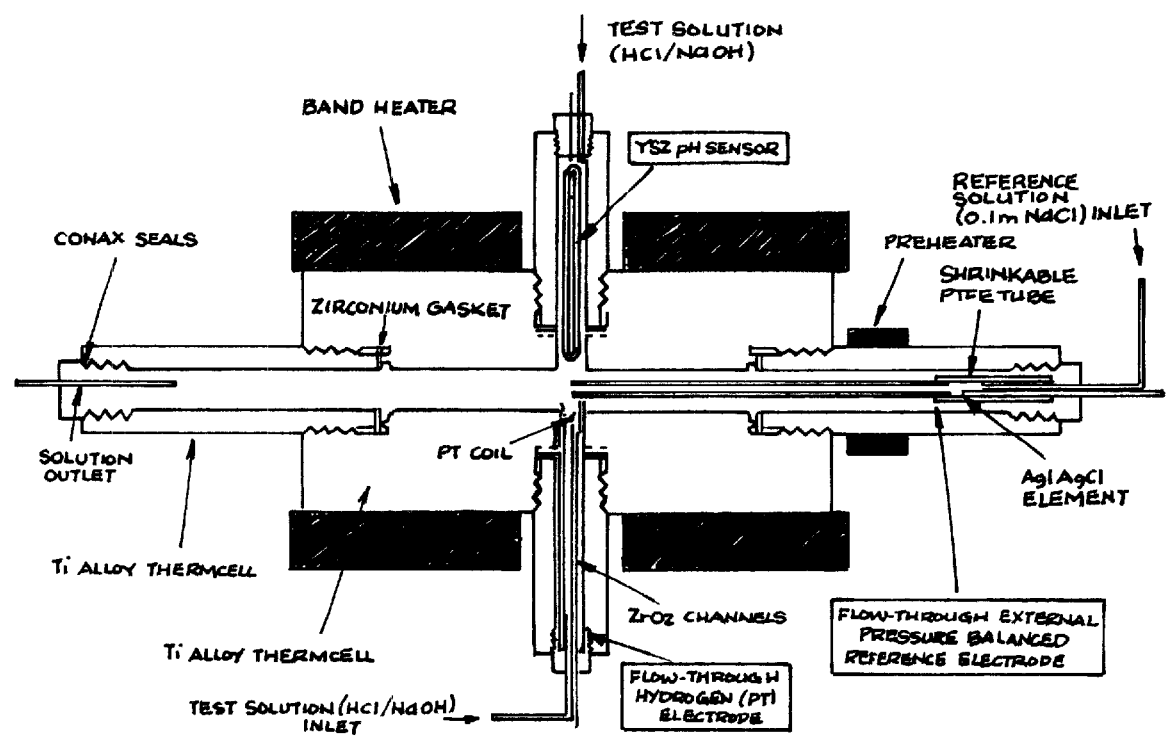
FIG. 4 is schematic of a thermocell for high temperature tests using the present invention.
Figure 5:
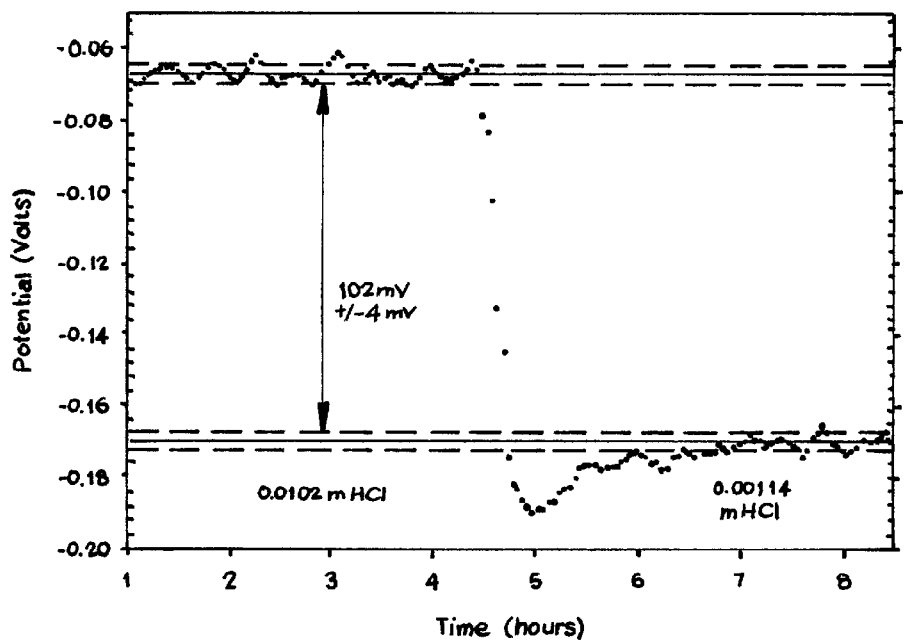
FIG. 5 is test data demonstrating the accuracy of the present invention.
Figure 6:
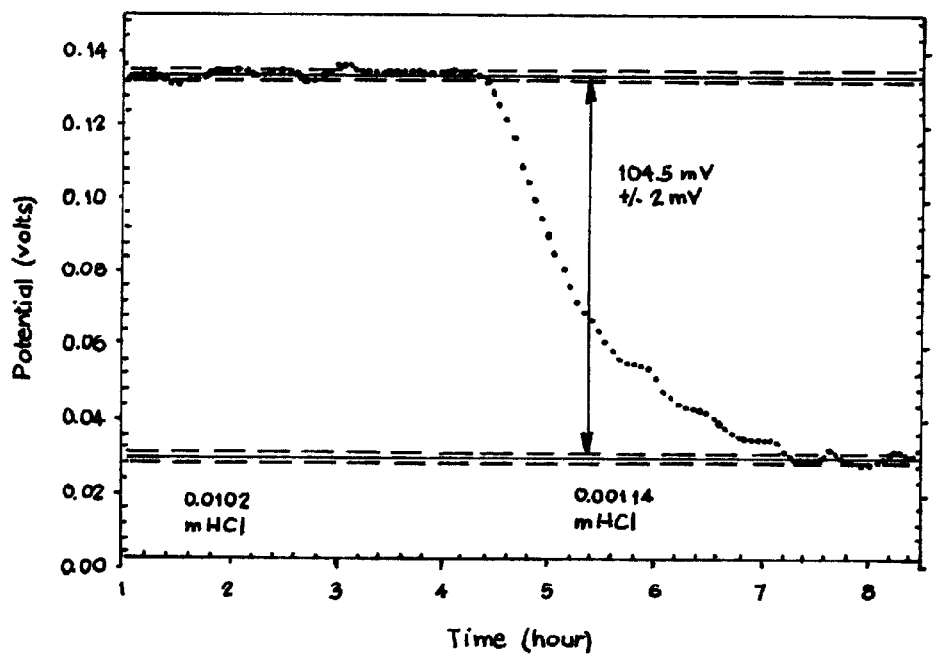
FIG. 6 is test data demonstrating the accuracy of the present invention.

FIG. 4 presents a schematic of a thermocell for high temperature tests in which YSZ pH sensing electrodes were tested together with a flow-through external pressure-balanced reference electrode (FTEPBRE) and a flow-through hydrogen (Pt) electrode (FTHE) at temperatures up to 350° C. and a pressure of 248 bars. It is known that if the dissolved hydrogen concentration is a constant, both FTHE and YSZ electrode should respond identically to the pH of test solutions. The test data is given in FIGS. 5 and 6 demonstrate that YSZ operates correctly under the test conditions for a long period of time, noting that the potential differences for two solutions are almost the same for the YSZ electrode and the hydrogen electrode.

While different embodiments of the invention has been described in detail herein, it will be appreciated by those skilled in the art that various modifications and alternatives to the embodiments could be developed in light of the overall teachings of the disclosure. Accordingly, the particular arrangements are illustrative only and are not limiting as to the scope of the invention which is to be given the full breadth of any and all equivalents thereof.

We claim:

1. A method of making a yttria-stabilized zirconia electrode having a ceramic tube, the improvement comprising:
   a. replacing the method of sealing the electrode with an epoxy seal and filling the tube with a ceramic glue without completely filling the tube;
   b. removing partially an area of cover on a wire in an area between a top of the ceramic glue and a top of the tube;
   c. adding a sealing glue above the top of the ceramic glue that adheres to the wire at the removed area of the cover, adheres to the tube and seals the top of the tube.

2. The method of claim 1, further including gripping an outside portion of the wire which extends beyond the top of the tube with a tube fitting used for gripping the tube.

3. The method of claim 1, wherein said ceramic glue is added in a small amount and the ceramic glue is heated in the tube before a next small amount of ceramic glue is added, until the final amount of ceramic glue is added and the tube is again heated.

4. The method of claim 3, wherein said ceramic glue is filled and heated in the tube using the following the steps: 1) add one centimeter of cement; 2) preheat the tube at 120° C. for 24 hours; 3) heat the tube at 600° C. for 5 hours; 4) add another centimeter of cement; 5) preheat the tube at 120° C. for 24 hours; and 6) heat the tube at 600° C. for 5 hours.

5. The method of claim 1, wherein the sealing glue is a glue which adheres to polymers and ceramics.

6. The method of claim 1, wherein the cover on the wire is removed using active sodium applied in the area to be removed.

7. A yttria-stabilized zirconia electrode comprising:
   a ceramic tube having a bottom with a closed tip and an open top;
   a wire having a cover that is inserted into said open top, whereby an end of said wire is exposed, said end being positioned in said closed tip and whereby a portion along said wire is exposed in an area within said tube and near said open top;
   sand which partially fills said tube;
   a ceramic glue filled above said sand, whereby said ceramic glue is inserted and heated in said tube in increments to a height in said tube which is below said portion of said wire which is exposed;
   a sealing glue filling the tube above said ceramic glue and adhering to said portion of said wire which is exposed.

8. The yttria-stabilized zirconia electrode of claim 7, further including a tube fitting griping said covered wire extending from said open top of said tube.

9. The yttria-stabilized zirconia electrode of claim 7, wherein said ceramic glue is filled and heated in the tube using the following the steps: 1) add one centimeter of cement; 2) preheat the tube at 120° C. for 24 hours; 3) heat the tube at 600° C. for 5 hours; 4) add another centimeter of cement; 5) preheat the tube at 120° C. for 24 hours; and 6) heat the tube at 600° C. for 5 hours.

10. The yttria-stabilized zirconia electrode of claim 7, wherein said sand is zirconia.

11. The yttria-stabilized zirconia electrode of claim 7, wherein said cover of said wire is a shrinkable polytetrafluoroethylene tube.

12. The yttria-stabilized zirconia electrode of claim 7, wherein said closed tip of said tube is filled Hg|HgO paste.

13. The yttria-stabilized zirconia electrode of claim 7, wherein said wire is a platinum wire.

14. The yttria-stabilized zirconia electrode of claim 7, wherein said sealing glue is a glue which adheres to polymers and ceramics.

15. The method of making a yttria-stabilized zirconia electrode comprising:
   a. inserting a wire into an open top of a ceramic tube having a closed tip, said wire having a cover, whereby an end of said wire is exposed, said end being positioned in said closed tip and whereby a portion along said wire is exposed in an area within said tube and near said open top;
   b. filling said tube partially with sand;
   c. filling said tube above said sand with a ceramic glue, whereby said ceramic glue is inserted and heated in said tube in increments to a height in said tube which is below said portion of said wire which is exposed;
   d. filling said tube with a sealing glue above said ceramic glue, whereby said sealing glue adheres to said portion of said wire which is exposed and adheres to said tube.

16. The method of claim 15, further including griping said wire extending from said open top of said tube with a connector means which grips and seals said tube.

17. The method of claim 15, wherein said sand is zirconia.

18. The method of claim 15. wherein said cover of said wire is a shrinkable polytetrafluoroethylene tube.

19. The method of claim 15, wherein said closed tip of said tube is filled Hg|HgO paste.

20. The method of claim 15, wherein said wire is a Platinum wire.

21. The method of claim 15, wherein said sealing glue is a glue which adheres to polymers and ceramics.

22. The method of claim 15, wherein said ceramic glue is filled and heated in the tube using the following the steps: 1) add one centimeter of cement; 2) preheat the tube at 120° C. for 24 hours; 3) heat the tube at 600° C. for 5 hours; 4) add another centimeter of cement; 5) preheat the tube at 120° C. for 24 hours; and 6) heat the tube at 600° C. for 5 hours.

* * * * *

UNITED STATES PATENT AND TRADEMARK OFFICE
CERTIFICATE OF CORRECTION

PATENT NO. : 6,517,694 B1
DATED : February 11, 2003
INVENTOR(S) : Zhou et al.

It is certified that error appears in the above-identified patent and that said Letters Patent is hereby corrected as shown below:

Column 1,
Line 7, please insert the following -- This invention was made with support from the Government under NSF Grant No. 9725191 and DOE Grant No. DE-FG07-96ER62303. The Government has certain rights in the invention. --

Signed and Sealed this

Twenty-first Day of June, 2005

JON W. DUDAS
*Director of the United States Patent and Trademark Office*